United States Patent
Yao et al.

(12)

(10) Patent No.: US 12,156,639 B1
(45) Date of Patent: Dec. 3, 2024

(54) CURVED ELECTRIC LARYNGOSCOPE

(71) Applicant: PEKING UNIVERSITY THIRD HOSPITAL (THE THIRD CLINICAL MEDICAL SCHOOL OF PEKING UNIVERSITY), Beijing (CN)

(72) Inventors: Youxiu Yao, Beijing (CN); Bin Han, Beijing (CN); Jiechu Wang, Beijing (CN); Jun Wang, Beijing (CN); Xiangyang Guo, Beijing (CN)

(73) Assignee: PEKING UNIVERSITY THIRD HOSPITAL (THE THIRD CLINICAL MEDICAL SCHOOL OF PEKING UNIVERSITY), Beijing (CN)

( * ) Notice: Subject to any disclaimer, the term of this patent is extended or adjusted under 35 U.S.C. 154(b) by 0 days.

(21) Appl. No.: 18/748,128

(22) Filed: Jun. 20, 2024

(30) Foreign Application Priority Data

Jan. 8, 2024 (CN) .......................... 202410023269.5

(51) Int. Cl.
  *A61B 1/267* (2006.01)
  *A61B 1/00* (2006.01)
  *A61B 1/005* (2006.01)

(52) U.S. Cl.
  CPC .......... *A61B 1/267* (2013.01); *A61B 1/00032* (2013.01); *A61B 1/00052* (2013.01);
  (Continued)

(58) Field of Classification Search
  CPC . A61B 1/267; A61B 1/00032; A61B 1/00052; A61B 1/00128; A61B 1/0052; A61B 1/0057
  (Continued)

(56) References Cited

U.S. PATENT DOCUMENTS 5,381,787 A * 1/1995 Bullard .................. A61B 1/042
  600/196
5,584,795 A * 12/1996 Valenti .................. A61B 1/267
  600/196

(Continued)

FOREIGN PATENT DOCUMENTS

CN    203987969 U    12/2014
CN    217510469 U    9/2022
  (Continued)

*Primary Examiner* — Eduardo C Robert
*Assistant Examiner* — David C Comstock
(74) *Attorney, Agent, or Firm* — Bayramoglu Law Offices LLC

(57) ABSTRACT

A curved electric laryngoscope is provided. The curved electric laryngoscope includes a handle and a display screen, where the display screen is rotationally provided at an upper part of the handle; a lower end of the handle is connected to a curved outer tube; the handle is provided therein with an inner tube and an inner tube position adjustment assembly; the inner tube includes an upper end connected to the inner tube position adjustment assembly and a lower end inserted into the curved outer tube; the inner tube position adjustment assembly includes a drive motor, a lead screw, a slide rail, a slider, and a slider bracket; the slide rail is provided along a length direction of the handle; and the lead screw is parallel to the slide rail; the drive motor is fixed at an upper end inside the handle.

6 Claims, 5 Drawing Sheets

(52) U.S. Cl.
CPC ........ *A61B 1/00128* (2013.01); *A61B 1/0052* (2013.01); *A61B 1/0057* (2013.01)

(58) Field of Classification Search
USPC ................ 600/185, 188, 190, 194, 196, 197
See application file for complete search history.

(56) References Cited

U.S. PATENT DOCUMENTS

| | | | | |
|---|---|---|---|---|
| 6,174,281 B1* | 1/2001 | Abramowitz | ........ | A61B 1/2673 |
| | | | | 600/199 |
| 7,946,981 B1 | 5/2011 | Cubb | | |
| 8,845,525 B2* | 9/2014 | McGrath | ................ | A61B 1/267 |
| | | | | 600/196 |
| 12,090,273 B1* | 9/2024 | Chauhan | ................ | G16H 30/40 |
| 2013/0274556 A1* | 10/2013 | Nearman | ........... | A61B 1/00045 |
| | | | | 600/187 |
| 2013/0310650 A1* | 11/2013 | Hales | ..................... | A61B 1/267 |
| | | | | 600/196 |
| 2014/0296645 A1* | 10/2014 | McGrath | ............ | A61B 1/00101 |
| | | | | 600/196 |
| 2020/0170498 A1 | 6/2020 | Galloway et al. | | |
| 2020/0178786 A1* | 6/2020 | Sabetrasekh | ....... | A61B 1/00073 |

FOREIGN PATENT DOCUMENTS

| | | |
|---|---|---|
| CN | 217744342 U | 11/2022 |
| CN | 115969298 A | 4/2023 |
| CN | 218832725 U | 4/2023 |
| CN | 220192981 U | 12/2023 |
| WO | 2022242951 A1 | 11/2022 |

\* cited by examiner

CURVED ELECTRIC LARYNGOSCOPE

CROSS-REFERENCE TO THE RELATED APPLICATIONS

This application is based upon and claims priority to Chinese Patent Application No. 202410023269.5, filed on Jan. 8, 2024, the entire contents of which are incorporated herein by reference.

TECHNICAL FIELD

The present disclosure relates to a laryngoscope, in particular to a curved electric laryngoscope, and belongs to the technical field of medical appliances.

BACKGROUND

Laryngoscopes mainly include direct laryngoscopes and indirect laryngoscopes. Direct laryngoscopes are an important instrument for tracheal intubation and widely used in anesthesia and emergency treatment, while indirect laryngoscopes are mainly used for examination of the throat in otolaryngology. The recently emerging visual laryngoscope can be considered as a type of indirect laryngoscope. Due to its convenient and fast use, high definition, and ease of protection for medical staff, the visual laryngoscope has gradually developed into a mainstream product for anesthesia and emergency intubation. In addition, the visual laryngoscope is increasingly popular in otolaryngology for the treatment of throat nodules and vocal cord tumors. Compared to straight-line support laryngoscopes, the visual laryngoscope is sometimes also referred to as a curved laryngoscope.

In clinical practice, difficult laryngeal exposure occurs due to common problems such as obesity, poor range of motion (ROM) of the cervical vertebra, and micrognathism, which poses a great challenge for tracheal intubation in anesthesiology and tumor treatment in otolaryngology. At present, there is a clinical difficulty for the existing video laryngoscope, that is, the camera position and angle are fixed, making it hard to effectively expose the field of view. Therefore, it is crucial to provide a visual laryngoscope that can adjust the position and angle of the field of view.

SUMMARY

In order to solve the technical problems in the prior art, an objective of the present disclosure is to provide a curved electric laryngoscope. The present disclosure can adjust the position and angle of the field of view, and can provide a wide field of view under the rigid support of a tongue depressor.

The present disclosure provides a curved electric laryngoscope, including a handle and a display screen, where the display screen is rotationally provided at an upper part of the handle; a lower end of the handle forms a curved connecting part; the curved connecting part is connected to a curved outer tube; the handle is provided therein with an inner tube and an inner tube position adjustment assembly; and the inner tube includes an upper end connected to the inner tube position adjustment assembly and a lower end inserted into the curved outer tube; and the inner tube position adjustment assembly includes a drive motor, a lead screw, a slide rail, a slider, and a slider bracket; the slide rail is provided along a length direction of the handle; the lead screw is parallel to the slide rail; the drive motor is fixed at an upper end inside the handle; an upper end of the lead screw is fixedly connected to an output shaft of the drive motor; the slider is provided on the slider bracket and connected to the slide rail in a sliding manner; one side of the slider bracket is provided with a threaded hole; and the lead screw is threaded to the slider bracket through the threaded hole.

In the curved electric laryngoscope, preferably, the one side of the slider bracket is provided with an inner tube mounting seat; the inner tube mounting seat is located at the same side as the threaded hole; an upper end of the inner tube is inserted into the inner tube mounting seat and forms an interference fit with the inner tube mounting seat.

In the curved electric laryngoscope, preferably, there are two grooved rollers rotationally arranged at an upper side of the inner tube mounting seat; an end of the inner tube is provided with a serpentine tube; the slider is connected to two pull wires; and the two pull wires are respectively wound on the two grooved rollers and enter the inner tube to connect the serpentine tube.

In the curved electric laryngoscope, preferably, an upper part inside the handle is fixedly provided with an upper limit switch, and a lower part inside the handle is provided with a lower limit switch; and the slider bracket includes a top provided with a first limit post and a bottom provided with a second limit post.

In the curved electric laryngoscope, preferably, the curved electric laryngoscope further includes an angle adjustment mechanism; the angle adjustment mechanism is connected to an upper end of the slide rail; the slide rail is cylindrical in shape; an outer wall of the slide rail is provided with two symmetrically arranged convex edges; and an inner wall of the slider is provided with two convex edge limit slots.

In the curved electric laryngoscope, preferably, the angle adjustment mechanism includes a limit frame, a connecting shaft, and an angle adjustment knob; the limit frame is fixed to the upper part inside the handle by a screw; a top of the handle is provided with a through-hole; the connecting shaft includes an upper end rotationally connected to the through-hole and a lower end rotationally connected to the limit frame; and the upper end of the connecting shaft is fixedly connected to the angle adjustment knob, while the lower end of the connecting shaft is fixedly connected to the upper end of the slide rail.

In the curved electric laryngoscope, preferably, the curved electric laryngoscope further includes an angle locking structure; the angle locking structure includes a lever, a first rotating shaft, a protrusion, a spring, a second rotating shaft, a rocker arm, and a ring gear; the ring gear is sleeved on the connecting shaft, and the ring gear and the connecting shaft form an interference fit; the first rotating shaft includes a top end fixedly connected to the lever and a lower end rotationally connected to the limit frame; the protrusion is fixed on the first rotating shaft; the second rotating shaft is fixed at a top of the limit frame; the rocker arm includes one end rotationally connected to the second rotating shaft and the other end forming a hooked part; the hooked part fits with the ring gear; and the spring includes one end fixedly connected to the rocker arm and the other end abutting against an inner wall of the handle.

In the curved electric laryngoscope, preferably, the angle adjustment mechanism includes an angle adjustment motor; the angle adjustment motor is fixed at a top inside the handle; and an output shaft of the angle adjustment motor is fixedly connected to a top end of the slide rail.

In the curved electric laryngoscope, preferably, the curved outer tube is clamped to a curved tongue depressor; one side of the tongue depressor forms a clamping plate with a side opening; a back of the display screen forms a battery compartment; and the battery compartment holds a lithium battery.

Compared with the prior art, in the present disclosure, the curved electric laryngoscope includes a handle and a display screen, where the display screen is rotationally provided at an upper part of the handle; a lower end of the handle forms a curved connecting part; the curved connecting part is connected to a curved outer tube; the handle is provided therein with an inner tube and an inner tube position adjustment assembly; and the inner tube includes an upper end connected to the inner tube position adjustment assembly and a lower end inserted into the curved outer tube. The present disclosure adjusts the position of the inner tube through the inner tube position adjustment assembly, such that the inner tube extends out of the curved outer tube or enters the curved outer tube, thereby changing the position of the field of view. Therefore, the present disclosure is applicable to patients with different glottic heights.

Figure 1:
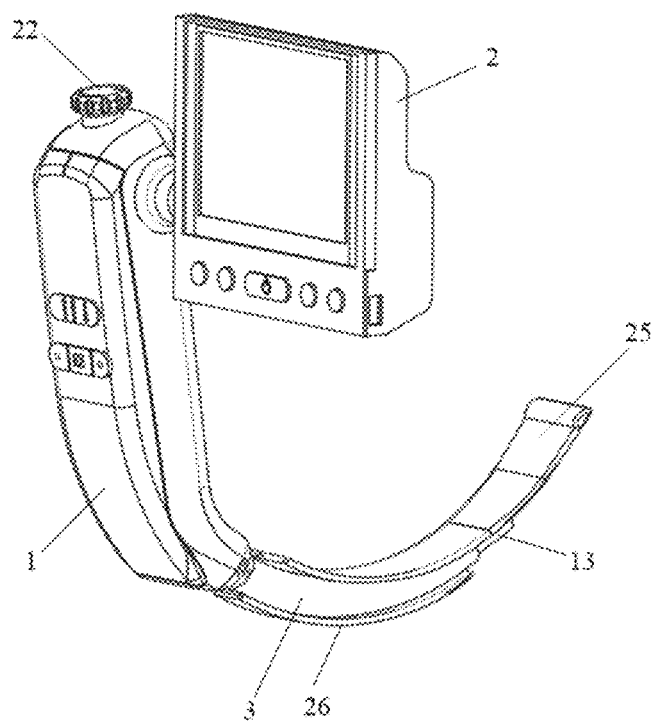
FIG. 1 is an isometric diagram of a curved electric laryngoscope according to Embodiment 1 of the present disclosure.

Reference Numerals: 1. handle; 2. display screen; 3. curved outer tube; 4. inner tube; 5. drive motor; 6. lead screw; 7. slide rail; 8. slider; 9. slider bracket; 10. threaded hole; 11. inner tube mounting seat; 12. grooved roller; 13. serpentine tube; 14. upper limit switch; 15. lower limit switch; 16. first limit post; 17. second limit post; 18. convex edge; 19. convex edge limit slot; 20. limit frame; 21. connecting shaft; 22. angle adjustment knob; 23. through-hole; 24. angle adjustment motor; 25. tongue depressor; 26. clamping plate with side opening; 27. battery compartment; 28. lithium battery; 29. control circuit board; 30. control button; 31. LCD screen; 32. screen control button; 33. lever; 34. first rotating shaft; 35. protrusion; 36. spring; 37. second rotating shaft; 38. rocker arm; 39. ring gear; and 40. soft skin moving structure.

DETAILED DESCRIPTION OF THE EMBODIMENTS

The embodiments of the present disclosure are described below in detail. Examples of the embodiments are shown in the drawings. The same or similar numerals represent the same or similar elements or elements having the same or similar functions throughout the specification. The embodiments described below with reference to the drawings are exemplary, and are only used to explain the present disclosure but should not be construed as a limitation to the present disclosure.

Embodiment 1 of the present disclosure provides a curved electric laryngoscope. As shown in FIGS. 1 to 6, the curved electric laryngoscope includes handle 1 and display screen 2. The display screen 2 is rotationally provided at an upper part of the handle 1. A lower end of the handle 1 forms a curved connecting part. The curved connecting part is connected to curved outer tube 3. The handle 1 is provided therein with inner tube 4 and an inner tube position adjustment assembly. An upper end of the inner tube 4 is connected to the inner tube position adjustment assembly, and a lower end of the inner tube 4 is inserted into the curved outer tube 3.

In this embodiment, the handle 1 includes a handle housing and a front cover plate. One side of the handle housing forms an open structure. The front cover plate is fixed to the open side of the handle housing by a screw. The front cover plate is provided with a button hole. An inner wall of the front cover plate is fixed to control circuit board 29. The control circuit board 29 is provided with control button 30. The curved outer tube 3 is integrated with the handle 1, and the inner tube 4 is made of soft plastic. The handle 1 is curved as a whole, and is connected to the curved outer tube 3 through the curved connecting part at the lower end of the handle 1. In this way, the connection position between the curved outer tube 3 and the handle 1 transitions smoothly, thereby reducing the movement resistance of the inner tube 4 and achieving smooth adjustment. Preferably, an end of the curved outer tube 3 is provided with soft skin moving structure 40. One end of the soft skin moving structure 40 is fixedly connected to an inner wall of the curved outer tube 3, and the other end of the soft skin moving structure 40 is fixedly connected to an outer wall of the inner tube 4. The soft skin moving structure 40 seals a gap between the curved outer tube 3 and the inner tube 4 to prevent liquid from entering, thereby playing a role of waterproofing.

Specifically, the inner tube position adjustment assembly includes drive motor 5, lead screw 6, slide rail 7, slider 8, and slider bracket 9. The slide rail 7 is provided along a length direction of the handle 1. The lead screw 6 is parallel to the slide rail 7. The drive motor 5 is fixed at an upper end inside the handle 1. An output shaft of the drive motor 5 is facing downwards. An upper end of the lead screw 6 is fixedly connected to the output shaft of the drive motor 5. The slider 8 is provided on the slider bracket 9, and the slider 8 is provided with a mounting hole. The slider 8 is provided on the slide rail 7 in a sliding manner through the mounting hole. The slider 8 is movable on the slide rail 7. One side of the slider bracket 9 is provided with threaded hole 10. An axis of the threaded hole 10 is parallel to the slide rail 7. The lead screw 6 is threaded to the slider bracket 9 through the threaded hole 10.

The drive motor 5 is configured to drive the lead screw 6 to rotate forward or reverse. When the lead screw 6 rotates, the vertical position of the slider bracket 9 is adjusted by threading it to the threaded hole 10. The function of the slide rail 7 is to limit the rotational freedom of the slider bracket 9, such that slider bracket 9 can only move axially on the slide rail 7 without rotating around the slide rail 7. The slider bracket 9 is configured to mount the slider 8, so as to move the slider 8 along the slide rail 7 and rotate the slider 8 on the slider bracket 9.

Furthermore, the one side of the slider bracket 9 is provided with inner tube mounting seat 11. The inner tube mounting seat 11 is located at the same side as the threaded hole 10. The upper end of the inner tube 4 is inserted into the inner tube mounting seat 11 and forms an interference fit with the inner tube mounting seat 11. There are two grooved rollers 12 rotationally arranged at an upper side of the inner tube mounting seat 11. An end of the inner tube 4 is provided with serpentine tube 13. The slider 8 is connected to two pull wires. The two pull wires are respectively wound on the two grooved rollers 12 and enter the inner tube 4 to connect the serpentine tube 13.

For the convenience of fixing the pull wires to the slider 8, there is a pull wire connection hole on a side wall of the slider 8. The function of the two grooved rollers 12 is to change the directions of the pull wires, such that the direction of the pull wires is changed from horizontal to vertical. In addition, the grooved rollers 12 also contribute to the smooth movement of the pull wires. It should be noted that the serpentine tube 13 is a prior art and can be purchased directly. This embodiment preferably adopts a serpentine tube controlled by two pull wires. Of course, a serpentine tube controlled by a single pull wire can also be used according to needs. A camera with a light source is provided inside the serpentine tube 13 (not shown in the figure). The camera with a light source is a commercially available component and can be purchased directly. The camera with a light source is electrically connected to the control circuit board 29.

Furthermore, an upper part inside the handle 1 is fixedly provided with upper limit switch 14, and a lower part inside the handle 1 is provided with lower limit switch 15. A top of the slider bracket 9 is provided with first limit post 16. A bottom of the slider bracket 9 is provided with second limit post 17. The first limit post 16 and the second limit post 17 are arranged coaxially.

When the first limit post 16 contacts the upper limit switch 14, the slider 8 moves to an upper limit position. At this point, the drive motor 5 stops working to prevent damage to the drive motor 5. When the second limit post 17 contacts the lower limit switch 15, the slider 8 moves to a lower limit position. At this point, the drive motor 5 stops working to prevent damage to the drive motor 5. The upper limit switch 14, the lower limit switch 15, and the drive motor 5 are electrically connected to the control circuit board 29.

Furthermore, the curved electric laryngoscope includes an angle adjustment mechanism. The angle adjustment mechanism is connected to an upper end of the slide rail 7. The slide rail 7 is cylindrical in shape. An outer wall of the slide rail 7 is provided with two symmetrically arranged convex edges 18. An inner wall of the slider 8 is provided with two convex edge limit slots 19. The convex edges 18 and the convex edge limit slots 19 ensure that the slider 8 rotates synchronously with the slide rail 7. If there is no convex edge 18, the slide rail 7 can only idle.

In this embodiment, the angle adjustment mechanism includes limit frame 20, connecting shaft 21, and angle adjustment knob 22. The limit frame 20 is fixed to the upper part inside the handle 1 by a screw. A top of the handle 1 is provided with through-hole 23. An upper end of the connecting shaft 21 is rotationally connected to the through-hole 23, and a lower end of the connecting shaft 21 is rotationally connected to the limit frame 20. The upper end of the connecting shaft 21 is fixedly connected to the angle adjustment knob 22, and the lower end of connecting shaft 21 is fixedly connected to the upper end of the slide rail 7.

The limit frame 20 is mainly configured to limit a position of the connecting shaft 21, such that the connecting shaft 21 rotates without axial displacement. The connecting shaft 21 is configured to connect the angle adjustment knob 22 and the slide rail 7, such that the slide rail 7 rotates following the rotation of the angle adjustment knob 22. When the slide rail 7 rotates, the slider 8 rotates synchronously. The control of the pull wires is achieved through the rotation of the slider 8. Thus, the pull wires can adjust the angle of the serpentine tube 13, thereby changing the angle of the field of view.

Furthermore, the curved outer tube 3 is clamped to tongue depressor 25. The tongue depressor 25 is a curved tongue depressor. One side of the tongue depressor 25 forms clamping plate 26 with a side opening. The tongue depressor 25 is clamped to the curved outer tube 3 through the clamping plate 26, which facilitates the mounting and removal of the tongue depressor 25. A back of the display screen 2 forms battery compartment 27. The battery compartment 27 holds lithium battery 28. A front of the display screen 2 is provided with liquid crystal display (LCD) screen 31 and screen control button 32. The display screen 2 is provided therein with a screen button circuit board. The screen control button 32 is connected to the screen button circuit board. The LCD display screen 31, the screen button circuit board, and the lithium battery 28 are electrically connected to the control circuit board 29.

It should be noted that in this embodiment, the tongue depressor 25 is only a preferred structure, and other structures that can fix the tongue depressor 25 to the curved outer tube 3 are also within the scope of protection of the present disclosure. For example, a mounting part is provided at one side of the tongue depressor 25, and is provided with a mounting hole. To use the tongue depressor 25, the curved outer tube 3 is directly inserted into the mounting hole of the mounting part.

Figure 7:
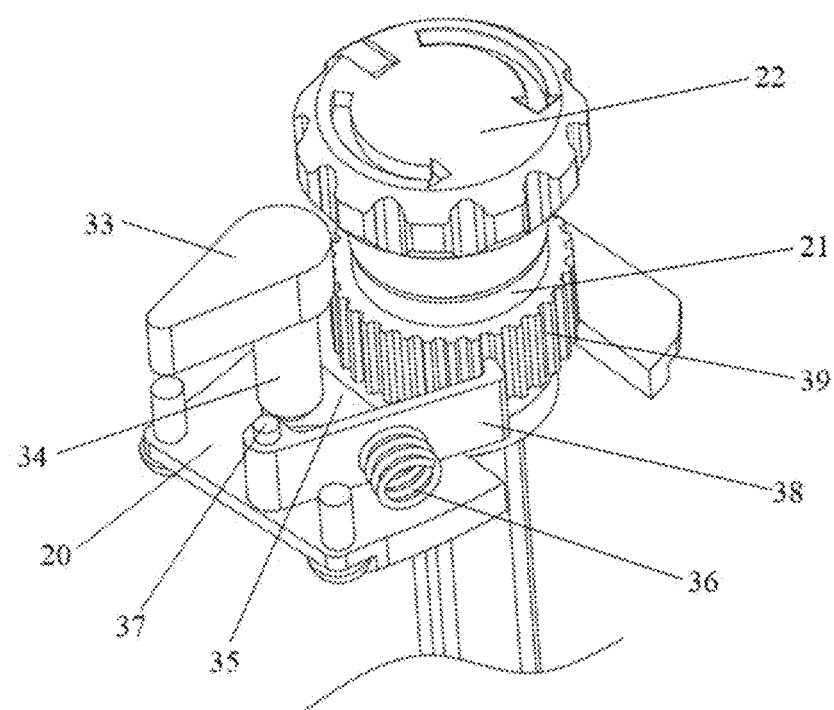
FIG. 7 is a structural diagram of an angle locking structure.
Figure 8:
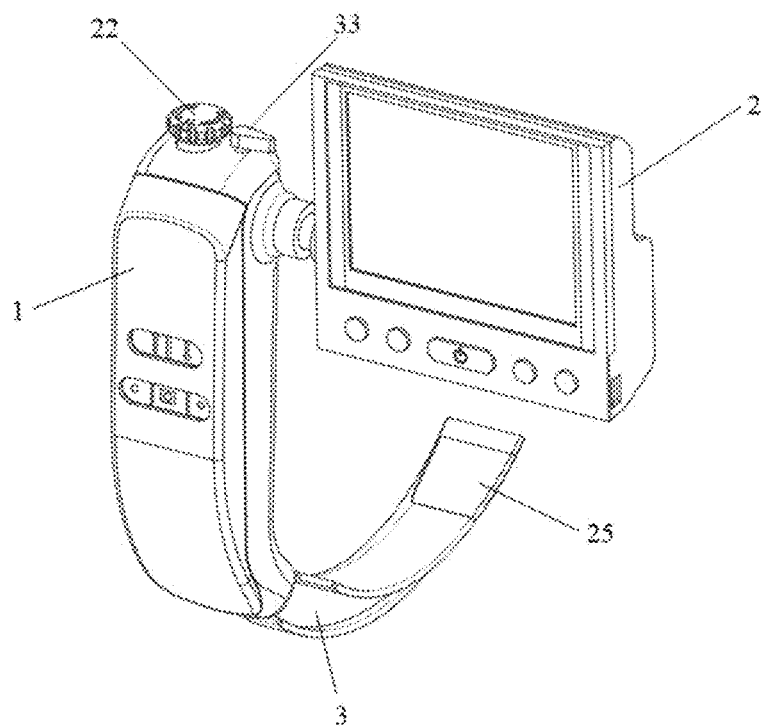
FIG. 8 is an isometric diagram of a curved electric laryngoscope according to Embodiment 2 of the present disclosure.

In Embodiment 1, after a user adjusts the angle of the serpentine tube 13 through the angle adjustment mechanism, the angle of the serpentine tube 13 is maintained by a friction resistance of the angle adjustment knob 22. In order to ensure that the serpentine tube 13 maintains a desired angle even when the hand is released after angle adjustment, Embodiment 2 of the present disclosure adds an angle locking structure on the basis of Embodiment 1. Referring to FIGS. 7 and 8, in Embodiment 2, the angle locking structure includes lever 33, first rotating shaft 34, protrusion 35, spring 36, second rotating shaft 37, rocker arm 38, and ring gear 39. The ring gear 39 is sleeved on the connecting shaft 21, and the ring gear and the connecting shaft form an interference fit. A top of the first rotating shaft 34 is fixedly connected to the lever 33, and a lower end of the first rotating shaft 34 is rotationally connected to the limit frame 20. It should be noted that the top of the handle 1 is provided with a through-hole for the first rotating shaft 34 to pass through. The protrusion 35 is fixed on the first rotating shaft 34. The second rotating shaft 37 is fixed at a top of the limit frame 20. One end of rocker arm 38 is rotationally connected to the second rotating shaft 37, and the other end of the rocker arm 38 forms a hooked part. The hooked part fits with the ring gear 39. One end of the spring 36 is fixedly connected to the rocker arm 38, and the other end of the spring 36 abuts against an inner wall of the handle 1.

The working principle of the angle locking structure is as follows. When it is necessary to lock the angle of the serpentine tube 13, the lever 33 and the first rotating shaft 34 cause the protrusion 35 to rotate, and the protrusion 35 does not come into contact with the rocker arm 38. Under an elastic force of the spring 36, the hooked part at the end of the rocker arm 38 engages with teeth of the ring gear 39, preventing the ring gear 39 from rotating and limiting the connecting shaft 21. Thus, the connecting shaft 21 cannot rotate, such that the slide rail 7 cannot rotate. In this way, the angle of the serpentine tube 13 is fixed. When it is necessary to adjust the angle of the serpentine tube 13, the lever 33 and the first rotating shaft 34 cause the protrusion 35 to rotate, and the protrusion 35 abuts against the rocker arm 38. The protrusion 35 pushes the rocker arm 38 such that the rocker arm 38 rotates around the second rotating shaft 37. The hooked part at the end of the rocker arm 38 separates from the teeth of the ring gear 39. At this point, the angle of the serpentine tube 13 can be adjusted by the angle adjustment knob 22.

Figure 2:
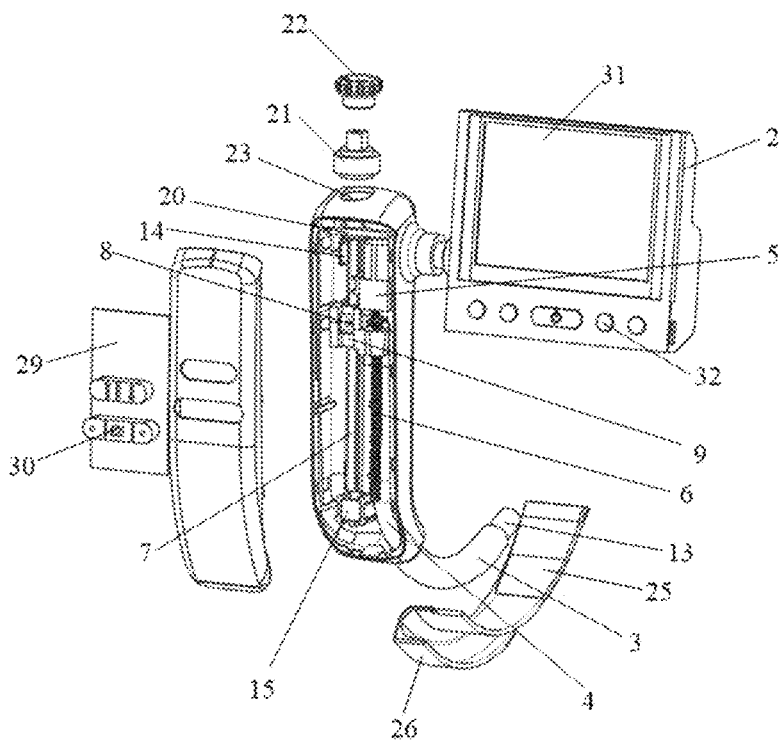
FIG. 2 is an exploded view of the curved electric laryngoscope shown in FIG. 1.
Figure 3:
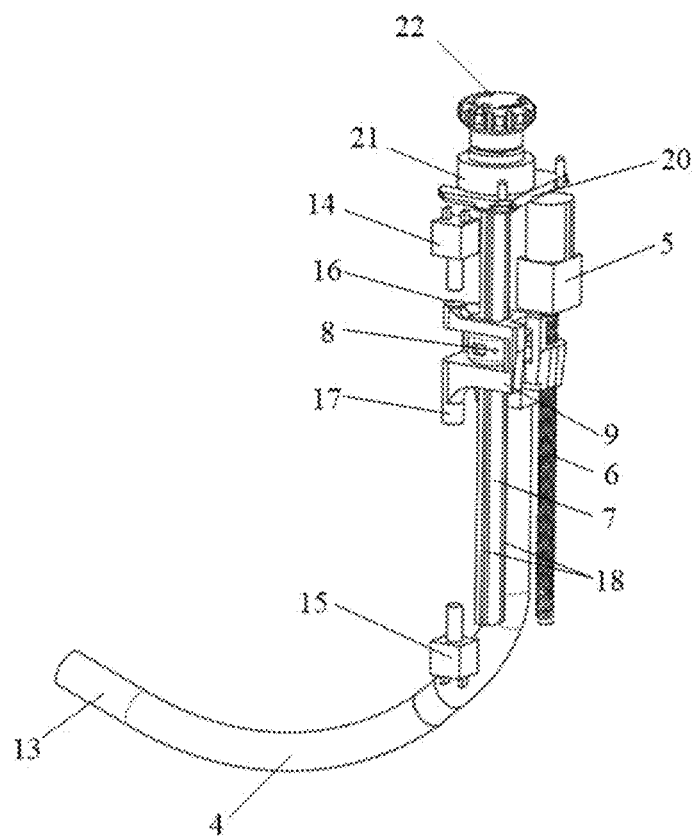
FIG. 3 is an internal structural diagram of the curved electric laryngoscope according to Embodiment 1 of the present disclosure.
Figure 4:
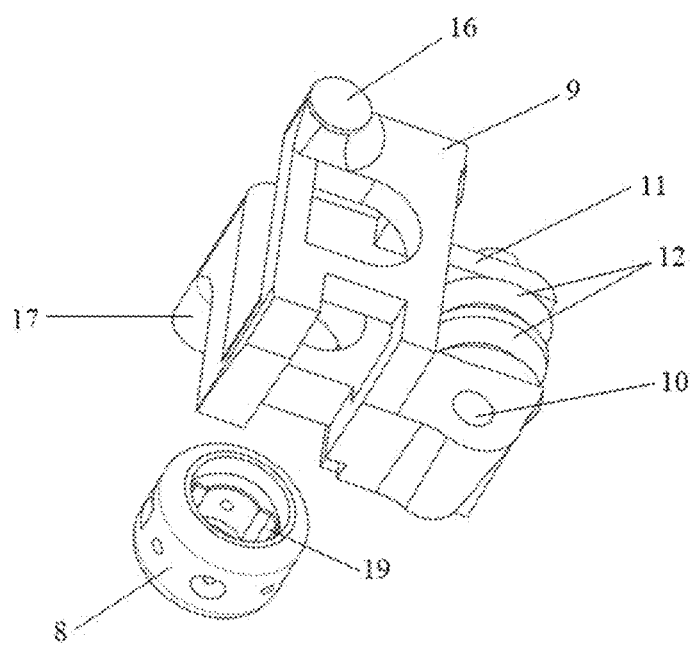
FIG. 4 is a structural diagram of a slider and a slider bracket.
Figure 5:
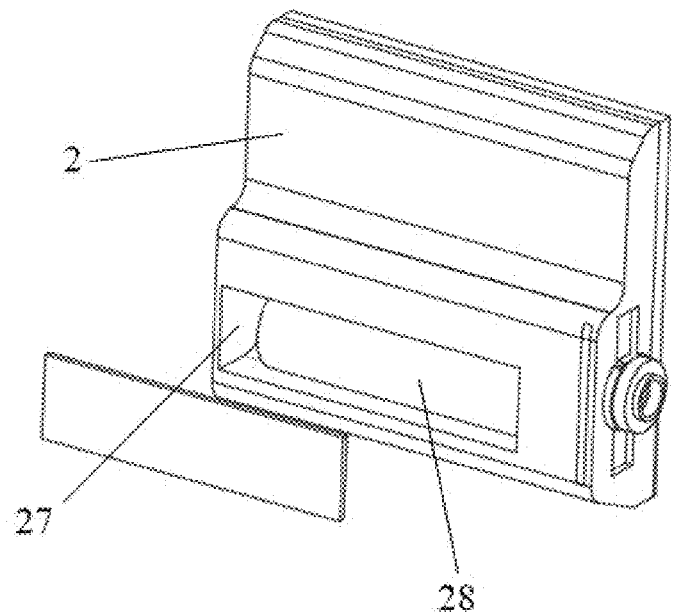
FIG. 5 is a structural diagram of a back of a display screen.
Figure 6:
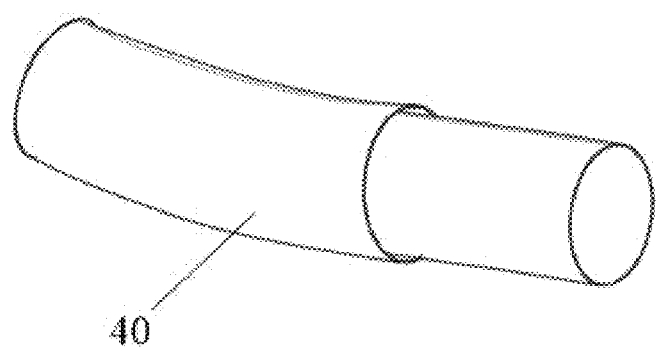
FIG. 6 is an isometric diagram of a soft skin moving structure.
Figure 9:
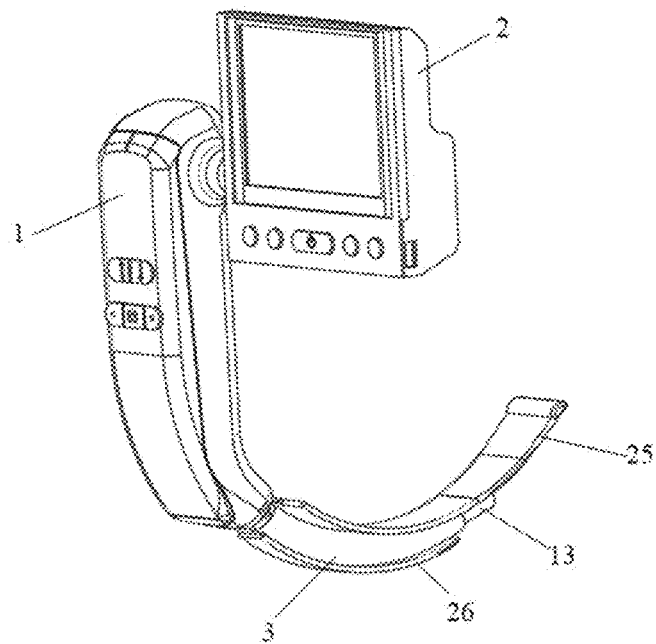
FIG. 9 is an isometric diagram of a curved electric laryngoscope according to Embodiment 3 of the present disclosure.
Figure 10:
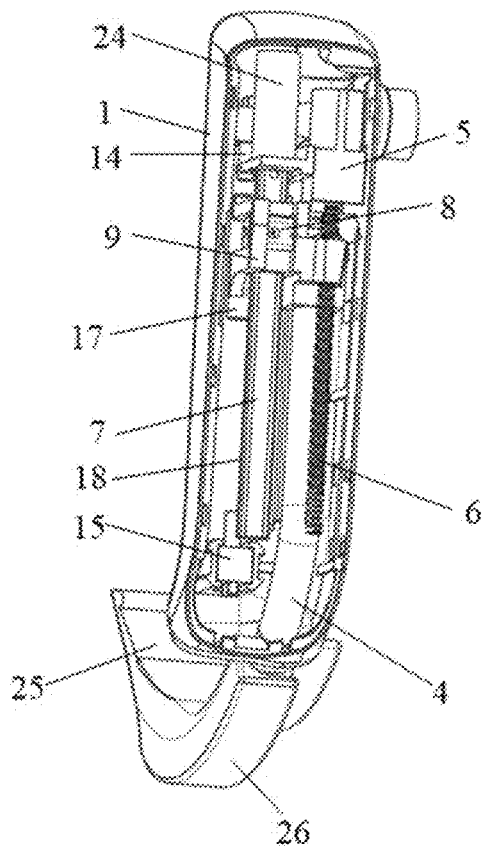
FIG. 10 is an internal structural diagram of the curved electric laryngoscope according to Embodiment 3 of the present disclosure.

Referring to FIGS. 9, 10, and 2, Embodiment 3 of the present disclosure differs from Embodiment 1 in that it adopts a different angle adjustment mechanism. In this embodiment, the angle adjustment mechanism includes angle adjustment motor 24. The angle adjustment motor 24 is fixed at a top inside the handle 1. An output shaft of the angle adjustment motor 24 is fixedly connected to a top end of the slide rail 7. The angle adjustment motor 24 is electrically connected to the control circuit board 29. The angle adjustment motor 24 rotates to drive the rotation of the slide rail 7. Embodiment 1 adopts manual control, while this embodiment adopts electric control.

The working principle of the present disclosure is as follows. In the present disclosure, the control button 30 on the handle 1 is configured to control the forward and reverse rotation of the drive motor 5 and the forward and reverse rotation of the angle adjustment motor 24. The screen control button 32 on the display screen 2 is configured to adjust screen brightness, camera brightness, and camera focus. The adjustment principle of the inner tube 4 is as follows. By operating the control button 30, the control circuit board 29 sends a work instruction to the drive motor 5. When the drive motor 5 rotates, it drives the lead screw 6 to rotate. The lead screw 6 fits with the threaded hole 10 to drive the slider bracket 9 to move on the slide rail 7. When the slider bracket 9 moves upwards (i.e. close to the drive motor 5), the slider bracket 9 moves upwards with the inner tube 4. The end of the inner tube 4 with the serpentine tube 13 gradually enters the curved outer tube 3 until the first limit post 16 on the slider bracket 9 contacts the upper limit switch 14. The slider bracket 9 moves to the upper limit position. The upper limit switch 14 sends an electrical signal to the control circuit board 29. At this point, even if the upward moving control button 30 is pressed again, the drive motor 5 will not rotate. When the slider bracket 9 moves downwards (i.e. away from the drive motor 5), the slider bracket 9 pushes the inner tube 4 downwards, causing the inner tube 4 to move downwards. The end of the inner tube 4 with the serpentine tube 13 extends out of the curved outer tube 3 until the second limit post 17 on the slider bracket 9 contacts the lower limit switch 15. The slider bracket 9 moves to the lower limit position, and the lower limit switch 15 sends an electrical signal to the control circuit board 29. At this point, even if the downward moving control button 30 is pressed again, the drive motor 5 will not rotate. In the present disclosure, the inner tube position adjustment assembly is located inside the handle 1, simplifying the internal structure of the inner tube 4. The inner tube 4 only includes a camera and wiring, thereby reducing the diameter of the inner tube 4. In addition, the inner tube position adjustment assembly is located inside handle 1 to increase the adjustable stroke and extension the length of the inner tube 4, thereby expanding its applicability.

The working principle of angle adjustment is as follows. The present disclosure provides two angle adjustment structures, which are introduced as follows. For the structural form in Embodiment 1, when adjusting the camera angle, only the angle adjustment knob 22 needs to be rotated. When the angle adjustment knob 22 is rotated, the connecting shaft 21 rotates. The connecting shaft 21 rotates with the slide rail 7. The convex edges 18 on the slide 7 fit with the convex edge limit slots 19 on the slider 8. When the slide rail 7 rotates, the slider 8 rotates synchronously. When the slider 8 rotates, it drives one of the two pull wires to retract and the other to release. In this way, the two pull wires control the angle change of the serpentine tube 13. Due to the angle change of the serpentine tube 13, the angle of the camera inside the serpentine tube is changed, thereby changing the angle of the field of view. For the structural form of Embodiment 2, when adjusting the angle of the serpentine tube 13, the control button 30 is pressed down. The control circuit board 29 controls the angle adjustment motor 24 to operate. The angle adjustment motor 24 rotates with the slide rail 7. When the slide rail 7 rotates, the slider 8 rotates synchronously. When the slider 8 rotates, it drives one of the two pull wires to retract and the other to release. In this way, the two pull wires control the angle change of the serpentine tube 13. Due to the angle change of the serpentine tube 13, the angle of the camera inside the serpentine tube is changed, thereby changing the angle of the field of view.

The above embodiments based on the schematic diagrams provide a detailed explanation of the structure, features, and effects of the present disclosure. The above described are only preferred embodiments of the present disclosure and do not limit the patent scope of the present disclosure. Any changes or modifications made to the present disclosure according to the concept of the present disclosure without departing from the spirit defined by the specification and schematic diagrams are considered as equivalent embodiments and should fall within the scope of protection of the present disclosure.

What is claimed is:

1. A curved electric laryngoscope, comprising a handle and a display screen, wherein the display screen is rotationally provided at an upper part of the handle; a lower end of the handle forms a curved connecting part; the curved connecting part is connected to a curved outer tube; the handle is provided therein with an inner tube and an inner tube position adjustment assembly; and the inner tube comprises an upper end connected to the inner tube position adjustment assembly and a lower end inserted into the curved outer tube;

the inner tube position adjustment assembly comprises a drive motor, a lead screw, a slide rail, a slider, and a slider bracket; the slide rail is provided along a length direction of the handle; the lead screw is parallel to the slide rail; the drive motor is fixed at an upper end inside the handle; an upper end of the lead screw is fixedly connected to an output shaft of the drive motor; the slider is provided on the slider bracket and connected to the slide rail in a sliding manner; one side of the slider bracket is provided with a threaded hole; and the lead screw is threaded to the slider bracket through the threaded hole;

the one side of the slider bracket is provided with an inner tube mounting seat; the inner tube mounting seat is located at the same side as the threaded hole; an upper end of the inner tube is inserted into the inner tube mounting seat and forms an interference fit with the inner tube mounting seat;

there are two grooved rollers rotationally arranged at an upper side of the inner tube mounting seat; an end of the inner tube is provided with a serpentine tube; the slider is connected to two pull wires; and the two pull wires are respectively wound on the two grooved rollers and enter the inner tube to connect the serpentine tube; and the curved electric laryngoscope further comprises an angle adjustment mechanism; the angle adjustment mechanism is connected to an upper end of the slide rail; the slide rail is cylindrical in shape; an outer wall of the slide rail is provided with two symmetrically arranged convex edges; and an inner wall of the slider is provided with two convex edge limit slots.

2. The curved electric laryngoscope according to claim 1, wherein an upper part inside the handle is fixedly provided with an upper limit switch, and a lower part inside the handle is provided with a lower limit switch;

the slider bracket comprises a top provided with a first limit post and a bottom provided with a second limit post;

when the first limit post contacts the upper limit switch, the slider moves to an upper limit position, and the drive motor stops working; and when the second limit post contacts the lower limit switch, the slider moves to a lower limit position, and the drive motor stops working.

3. The curved electric laryngoscope according to claim 2, wherein the angle adjustment mechanism comprises a limit frame, a connecting shaft, and an angle adjustment knob;

the limit frame is fixed to the upper part inside the handle by a screw;

a top of the handle is provided with a through-hole;

the connecting shaft comprises an upper end rotationally connected to the through-hole and a lower end rotationally connected to the limit frame; and the upper end of the connecting shaft is fixedly connected to the angle adjustment knob, while the lower end of the connecting shaft is fixedly connected to the upper end of the slide rail.

4. The curved electric laryngoscope according to claim 3, further comprising an angle locking structure, wherein the angle locking structure comprises a lever, a first rotating shaft, a protrusion, a spring, a second rotating shaft, a rocker arm, and a ring gear;

the ring gear is sleeved on the connecting shaft, and the ring gear and the connecting shaft form the interference fit;

the first rotating shaft comprises a top end fixedly connected to the lever and a lower end rotationally connected to the limit frame;

the protrusion is fixed on the first rotating shaft;

the second rotating shaft is fixed at a top of the limit frame;

the rocker arm comprises a first end rotationally connected to the second rotating shaft and a second end forming a hooked part;

the hooked part fits with the ring gear; and the spring comprises a first end fixedly connected to the rocker arm and a second end abutting against an inner wall of the handle.

5. The curved electric laryngoscope according to claim 2, wherein the angle adjustment mechanism comprises an angle adjustment motor; the angle adjustment motor is fixed at a top inside the handle; and an output shaft of the angle adjustment motor is fixedly connected to a top end of the slide rail.

6. The curved electric laryngoscope according to claim 2, wherein the curved outer tube is clamped to a curved tongue depressor; one side of the curved tongue depressor forms a clamping plate with a side opening; a back of the display screen forms a battery compartment; and the battery compartment holds a lithium battery.

* * * * *